(12) United States Patent
Kaundun

(10) Patent No.: US 7,892,742 B2
(45) Date of Patent: Feb. 22, 2011

(54) PCR SCREENING METHOD

(75) Inventor: Shiv Shankhar Kaundun, Mauritian (GB)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 12/305,506

(22) PCT Filed: Jun. 25, 2007

(86) PCT No.: PCT/GB2007/002352
§ 371 (c)(1),
(2), (4) Date: May 18, 2009

(87) PCT Pub. No.: WO2007/148119
PCT Pub. Date: Dec. 27, 2007

(65) Prior Publication Data
US 2009/0305269 A1 Dec. 10, 2009

(30) Foreign Application Priority Data
Jun. 27, 2006 (GB) .................................. 0612712.0

(51) Int. Cl.
*C12Q 1/68* (2006.01)
(52) U.S. Cl. .................. 435/6; 435/91.1; 435/91.2; 536/24.33
(58) Field of Classification Search .................. None
See application file for complete search history.

(56) References Cited

PUBLICATIONS

Schmitt-John, T. DE 10 2004 048 381. Apr. 2006., English translation.*
Kanae et al. J. Vet. Diag. vol. 17:258-262. 2005.*
Neff et al. Plant Journal vol. 14:387-392. 1998.*
Haliassos et al. Nucleic Acids Research vol. 17:3606. 1989.*
Kanae Yutaka et al: "A method for detecting complex veterbral malformation in Holstein calves using polymerase chain reaction-primer introduced restriction analysis." Journal of Veterinary Diagnostics Investigation Offical Publication of the American Association of Veterinary Laboratory Diagnosticians, Inc., May 2005, pp. 258-262, XP002448092, ISSN: 1040-6387.
Neff, Michael M. et al: dCAPS, a simple technique for the genetic analysis of single nucleotide polymorphisms; Experimental applications in Arabidposis thaliana genetics, Plant Journal, vol. 14, No. 3, May 1999, pp. 387-392, XP002284998, ISSN: 0960-7512.
Haliassos A et al: "Modification of Enzyatically Amplified DNA for the Detection of Point Mutations," Nucleic Acids Research, vol. 17, No. 9, 1989, p. 3606, XP002448095, ISSN: 0305-1048.
Ke Xiayi et al: "PIRA PCR designer for restriction analysis of single nucleotide polymorphisms," Bioinformatics (Oxford), vol. 17, No. 9, Sep. 2001, pp. 8380839, XP002448095, ISSN: 1367-4803.
Shi, M. W.: "Technologies for individual genotyping: Detection of genetic polymorphisms in drug targets and disease genes;" American Journal of Pharmacogenomics, vol. 2, No. 3, 2002, pp. 197-205, XP009065150, ISSN: 1175-2203.
Ke Xiayi et al: "PCR designer for restriction analysis of various types of sequence mutation." Bioinformatics (Oxford), vol. 18, No. 12, Dec. 2002, pp. 1688-1689, XP002448096, ISSN: 1367-4803.

* cited by examiner

*Primary Examiner*—Heather Calamita
(74) *Attorney, Agent, or Firm*—James Cueva

(57) ABSTRACT

A tooling system (1) having a number of elements (2) arranged in an array, which elements define a contoured surface, or a section of a contoured surface. The tooling system also including means (7) for mounting an element to a support rail (5) which extends across the array, which means allows adjustment of the height of the element with respect to other elements of the array, and extends through the support rail into a space defined below the support rail. A supporting element (6) formed from a suitable resistant material and including accommodation means (8) for the means for mounting, is located in the space below the support rail and is sized so that it substantially vertically fills the space between the support rail and a base on which the tooling system is located.

9 Claims, 4 Drawing Sheets

PCR SCREENING METHOD

Figure 1:
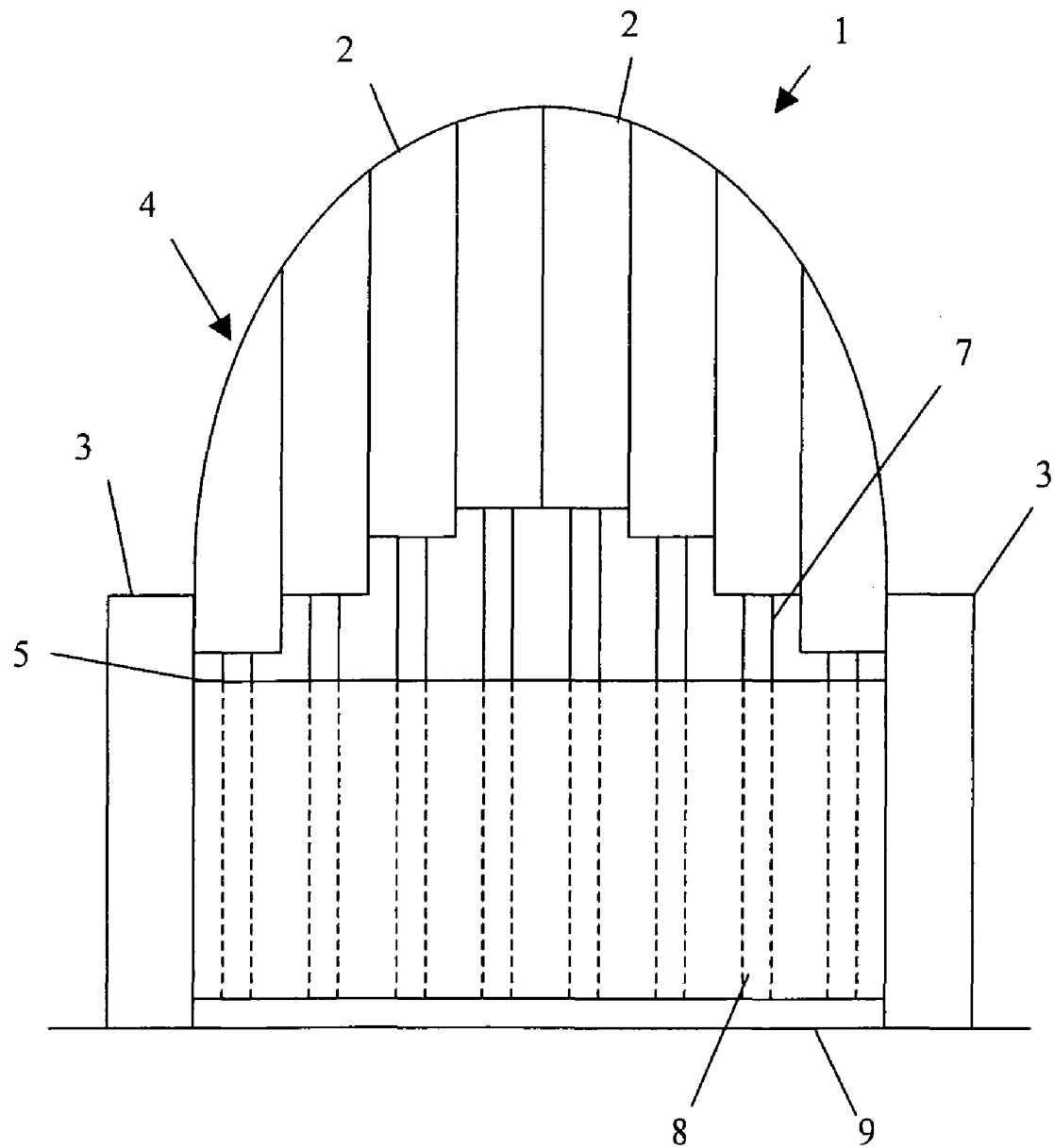

This application is a 371 of International Application No. PCT/GB2007/002352 filed Jun. 25, 2007, which claims priority to GB 0612712.0 filed Jun. 27, 2006, the contents of which are incorporated herein by reference.

The present invention relates to a component for use in a tooling system, and to an improved tooling system, including said component.

The component is particularly suitable for use in the tooling systems generally described and claimed in PCT Patent Publication No. WO 2002/064308. This Patent document provides a description of the base technology for a tooling system from which the invention of the current Patent Application is generated.

This PCT Patent Application describes a tooling system comprising a plurality of elements generally arranged in an array, each element of the array being moveable longitudinally of its length relative to the other elements of the array. The tooling system also includes means to adjust the longitudinal position of a respective element so that the array defines a desired surface contour; and means for retaining the elements in position. Each element of the array including a first end that is machinable and is removably mounted to a base portion and the elements are arranged so that the machinable portion of the/or each element can be machined to produce a desired surface contour. Further the elements of the array may be moved between a closed position in which the elements contact one another and are secured in position, and an open position in which the elements of the array are spaced apart to facilitate the machining of the machinable portion, and each element is capable of vertical movement relative to the surrounding elements. Drive means for opening and closing the array and elements with respect to support rails may be located in the space below the elements of the array.

The array may comprise the whole of the tooling surface or may comprise a section of the tooling surface with the whole tooling surface being made up of a number of the sections.

Within each array, or section of the array, the elements may be held in configuration by means of a bolster, for example of the type as described and claimed in co-pending Patent Publication No. WO 2005/61147.

The support rails supporting the elements in the array form a series of rails running across the array, or a section of the array. The support rails are supported at the edges of the array, or at the edges of the section, no support is provided for the support rails in the space below the array, or section. The support rails are formed from a substantial bar and have spaced settings for mounting and locating the individual elements of the array, or section. Consequently, the loading placed on the elements in use is transmitted through the mounting from the elements to the support rail.

The above-mentioned tooling system has a principal use in the production of moulding surfaces, for example, injection moulding surfaces. Typically, injection moulding may have an operating pressure or load in the region of 500 bar to 2000 bar and therefore a heavy loading will be placed on the moulding surface. With the present tooling system this loading, or pressure, will be transmitted through the elements of the array and the support systems. The support elements and the support rail will be placed under significant loading and this will mean a heavy load or bending force is applied to the support rail. The longer the support rail the higher is the bending force and the result could be that some deformation of the support rail leading to inaccuracies or anomalies in the mould surface. This, as will be appreciated, is not desirable.

The present invention is concerned with providing means to alleviate, or substantially eliminate, this problem.

In accordance with a first aspect of the present invention, there is provided a tooling system comprising a number of elements arranged in an array wherein one of the surfaces of the elements define a contoured surface, or a section of a contoured surface, and which tooling system also includes means for mounting an element to a support rail extending across the array and which means allows adjustment of the height of the element of the array with respect to the other elements of the array and the means for mounting extends through the support rail into a space defined below the support rail, wherein a supporting element formed from a suitable resistant material and including accommodation means for the means for mounting, is located in the space below the support rail and is sized so that it substantially vertically fills the space between the support rail and a base on which the tooling system is located.

The provision of the supporting element in the space so that it substantially vertically fills the space below the support rail or support rails, in effect means that the supporting element is an interference fit in the space, and that as loading is applied to the support rail, for example by the operation or use of the mould, the loading will be transmitted from the elements through the support rails to the supporting element and thereby to the base on which the tooling system is mounted. Therefore any tendency for deformation in the support rail or support rails is negated and any deformation nullified. Consequently, removing the deformation in the support rail or support rails and the mould surface will remain substantially as designed.

In one arrangement of the present invention the supporting element is formed as a single member. However, alternatively the supporting element may comprise a plurality of elements assembled together to form the supporting element. The supporting element may be divided into horizontal and/or vertical components. The components may be fixedly interconnected.

The selection of material from which the supporting element is formed is important and the selection will take into account several factors including the operating conditions as well as cost and formability. The most important factor is that the material is able to transmit the loading and pressure applied and does not simply fail when load is applied.

In one embodiment of the invention, the supporting element is formed from a resilient material, such as mild steel. Consequently, the element is readily machinable and inexpensive to produce. Alternatively, the supporting element may be formed from a resistant material such as polymer concrete. With this arrangement the supporting element can be readily cast and therefore formed to a net shape.

In one configuration it is envisaged that the supporting element will incorporate additional functions, for example, the supporting element may also be used as a heat exchanger to withdraw or provide heat to the tooling system as a whole. If this is the case the material selection for the supporting element will also take account of the thermal properties of the material, for example the coefficient of expansion and thermal conductivity, in order to ensure that the supporting element does not exert undue load on the system in operation In the conventional arrangement of the tooling system as described in the above mentioned PCT Patent Publication No. WO 2002/064308 the support rail and support rails support the loading and pressure transmitted from the elements during the operation of the tooling system. In one arrangement of the present invention the support rail, or selected support rails, of the tooling system may be extended downwardly to contact the base and so provide the supporting element. The support rail or rails may extended downwardly either as an integral member or alternatively by the addition of a secondary member fixedly located.

This arrangement of extending the support rail(s) may be used as an alternative to the provision of a supporting element or alternative as an additional supporting element.

The individual elements of the array are held in vertical alignment and position by means for mounting that connect the elements to the support rail or support rails. In one arrangement of the present invention, the means for mounting comprises a screw-threaded member that extends between the lower surface of one of the elements and a screw-threaded bore provided in the support rail or the support rails.

With this type of arrangement the screw threaded member will extend from the lower surface of a respective element, through the bore and into the space defined below the support rail or support rails Therefore, in one arrangement of the present invention, the supporting element is provided with a network of holes corresponding to the location of the means for mounting and the mounting provisions on the support rail or the support rails.

When the tool is assembled the screw-threaded members of the means for mounting are located in a respective hole. Further means may be provided in the hole to facilitate the adjustment of the height of the element in the array.

It is envisaged that the network of holes in the supporting element will enable some flexibility in the position of the elements in the array and therefore in operation there will be a number of spare holes that are not in use. The spare holes may be used to house ancillary equipment, for example actuators or sensors or means to expel the elements from the array.

Further the spare holes may be used to secure the supporting element to the support rail or support rails. The supporting element may be secured to the support rail or support rails by means of bolts located in countersunk bores in the supporting element and a respective support rail.

The upper surface of the supporting element may be shaped to facilitate the operation of the tooling system. The shape imparted to the upper surface may be sinusoidal, V-grooved, or castellated, either in one or two directions.

In one arrangement of the present invention the surface of the supporting element adjacent to the support rail or support rails is provided, with a series of grooves running side to side across the supporting element. The grooves may form a lattice that extends in one direction only or which extends in two directions. These grooved systems allow automatic adjustment of the elements to be provided.

Alternative arrangements of the supporting element include:

a series of tubular members, such as cylinders, that are formed into a lattice.

individual tubular members such as cylinders provided as individual members appropriately located with respect to the means for mounting.

a hollow box like member which may be filled with a suitable particulate material such as sand. This box like member may also include appropriately located tubular members such as cylinders.

The supporting element may be secured in position below the support rails with respect to the bolster that surrounds the array by suitable fixings. The fixings may comprise screw fixings that locate the supporting element with respect to a bolster that surrounds the elements of the array.

In accordance with a second aspect of the present invention, there is provided a supporting element for use with the apparatus of the first aspect of the present invention.

Figure 2B:
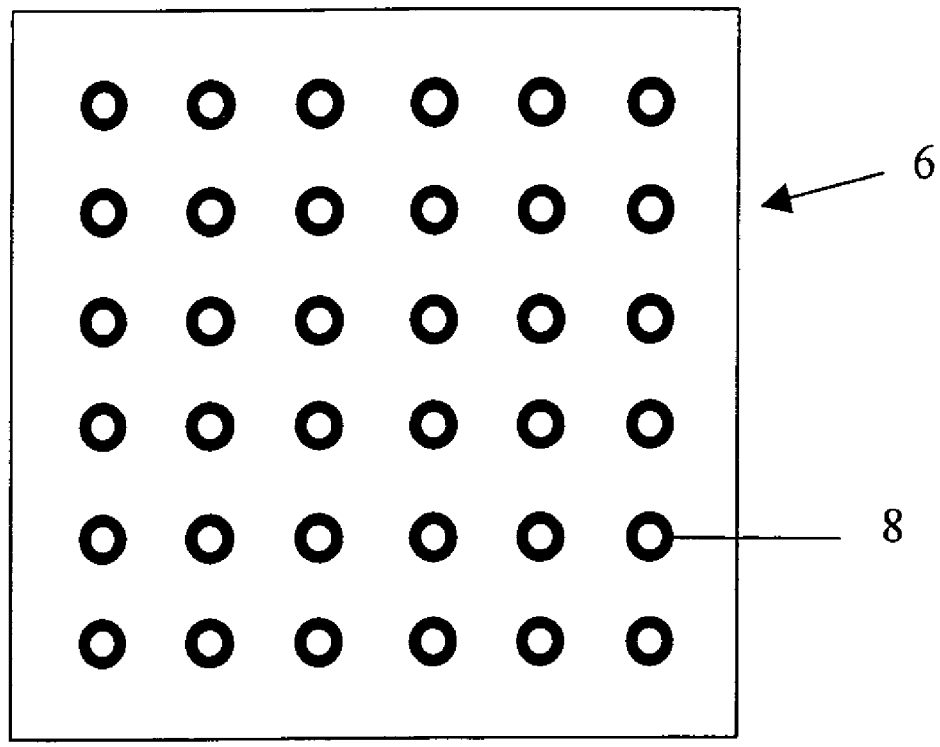
Figure 2A:
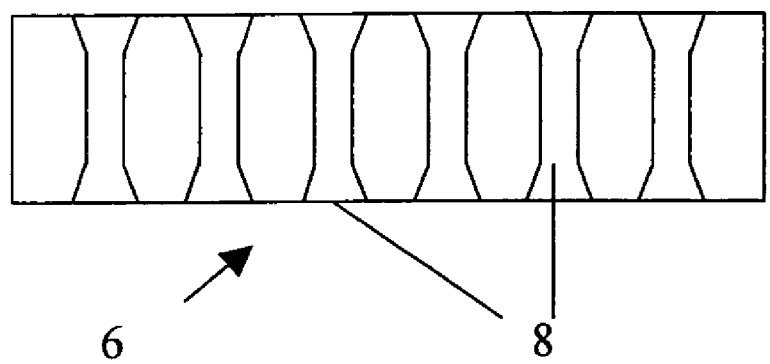
Figure 3A:
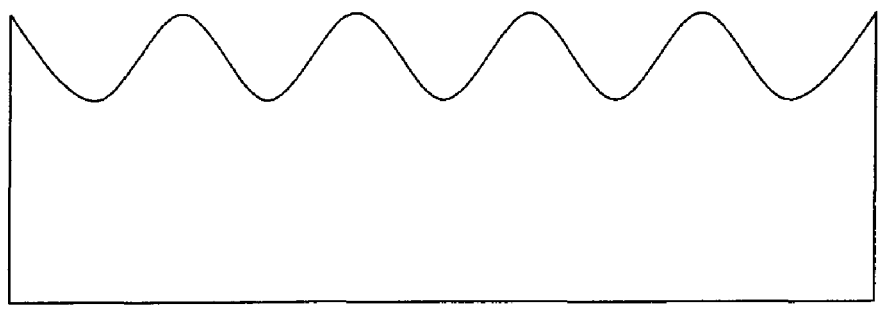
Figure 3B:
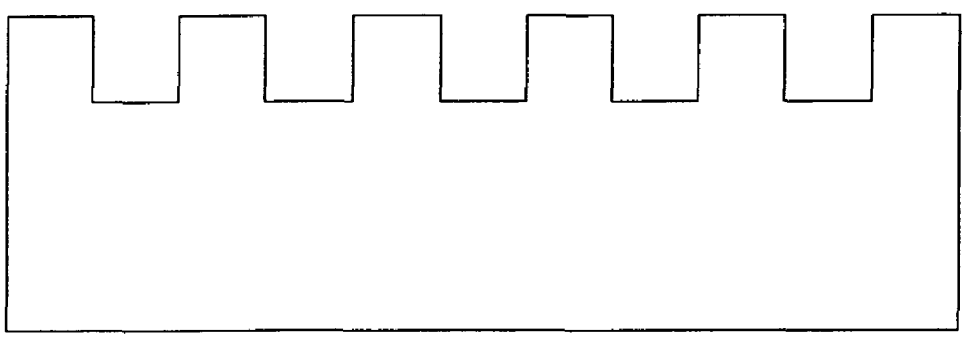
Figure 3C:
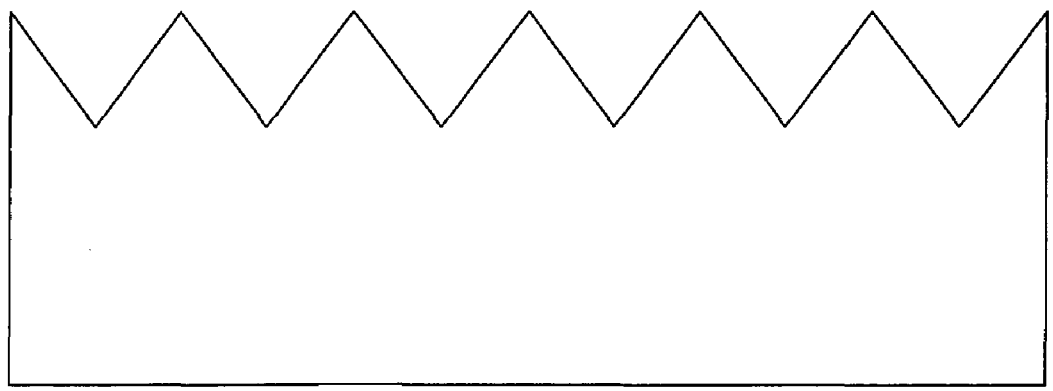
Figure 4:
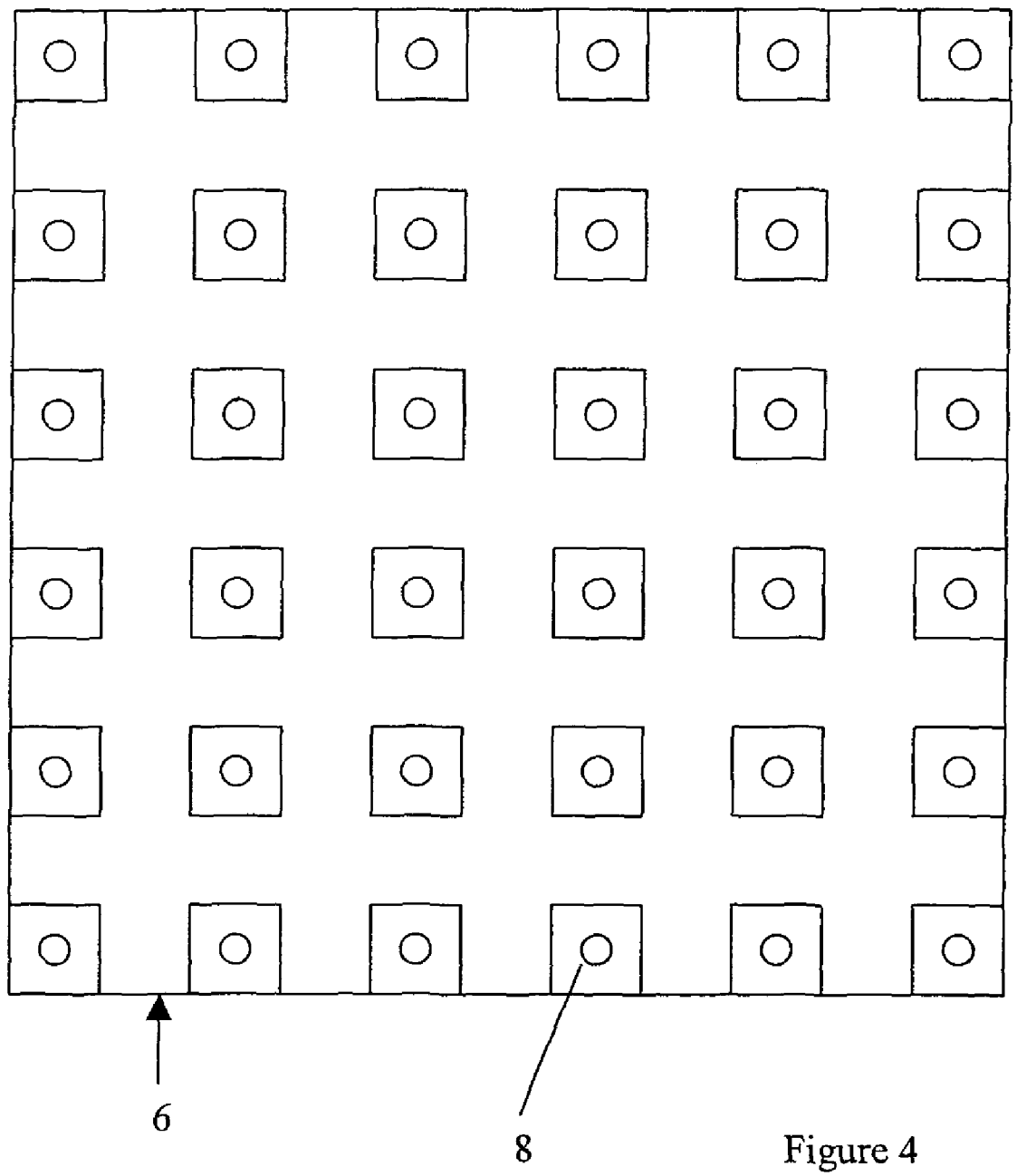

The invention will now be described by way of example, with reference to the accompanying drawings, in which:

FIG. 1 shows a schematic representation of a tooling system made in accordance with the present invention;

FIG. 2A+B show a schematic representation of a first supporting element made in accordance with the present invention;

FIG. 3A to 3C show schematic side views of alternative designs of supporting elements made in accordance with the present invention FIG. 4 shows a plan view a two directional embodiment of the alternate design shown in FIG. 3B.

Now referring to FIG. 1 of the drawings, there is shown a schematic representation of a tooling system generally in accordance with the present invention. The tooling system 1 comprises a number of elements 2 formed into an array and disposed between the peripheral sidewalls 3 of a bolster element.

Each of the elements 2 includes a machinable portion, the upper section of the element, and a fixed portion. The elements 2 of the array are mounted to support rails 5 which extend across the array between opposing sidewalls 3 of the bolster by means of screw threaded bolts 7.

The screw threaded bolts 7 are fixedly mounted to the fixed portion of the elements and is mounted in a screw threaded bore provided in the support rail 5.

A supporting element 6 is disposed in the space below the support rails 5 and rests on a base 9. The supporting element 6 also contacts the lower surface of the support rails 5 and is provided with a network of holes 8 corresponding to the mounting position for the elements of the array. The holes 8 are each provided at there ends with a counterbored sections 8a. The counterbored section enables the supporting element to be fixedly mounted to the support rail by a simple nut and bolt arrangement.

Further the supporting element may be provided with side holes (not shown) which enable the supporting element to be fixedly mounted to the bolster.

In operation, the elements 2 of the array, or a portion of the array, can be spread apart into an open position, in order to better facilitate adjustment of the position of the elements 2 with respect to each other, or machining of the machinable portion of the element. In this manner the elements of the array be machined individually without removal from the array if desired.

The operation of the array is disclosed fully in WO 2002/064308 which description is incorporated herein by reference.

In use, the upper surface of the elements 2 forms the contoured surface of a mould 4 such as an injection moulding mould. Load is applied during operation of the tooling system and this load is transmitted via the elements, support rails and supporting element to the base 9. The loading therefore does not apply a bending force to the support rail or support rails 5.

The supporting element 6 is shown in further detail in FIGS. 2A and 2B of the drawings there is shown a first design of supporting element 6 for location in the space below the support rail 5. The supporting element 6 is dimensioned so as to substantially fill the space below the support rails 5 and above the base and also to allow ready construction and operation of the other mechanical elements of the array.

The design of supporting element shown here is a straight forward supporting element formed as a simple block member, which is provided with a network of holes 8

When the tooling system is assembled the end section of the screw-threaded bolts 7 will extend through and below the support rails 5. The holes 8 in the supporting element are located so that the end section of a respective bolt 7 extends into the hole 8.

Now referring to FIG. 3 of the drawings, there is shown end views of alternative designs of supporting element 6. The locating and operation of these supporting elements is basically as described and FIG. 3 shows side views of alternate designs. The side views shown will be the same for the single direction embodiments and the two direction embodiments.

FIG. 4 shows a plan view of the alternate configuration shown in FIG. 3B and illustrates the two direction embodiment only.

Each of the alternate designs shown in FIGS. 3A to 3C and FIG. 4 are suitable for automatic operation of the tooling system.

The invention claimed is:

1. A method for detecting a point mutation in a gene of interest comprising:
   a) performing a PCR reaction on an extract of DNA obtained from a plant containing the gene of interest using a pair of PCR primers which are capable of amplifying the region surrounding and encompassing the mutation;
   b) digesting the PCR product of step (a) with at least one restriction enzyme, which differentiates between the wild type sequence and the sequence containing the mutation, in order to obtain a restriction digest;
   c) analysing the digested PCR product of step (b) in order to identify those DNA extracts indicative of the presence of the mutation;
   characterised in that (i) the 3' ends of the PCR primers are separated by 3 or fewer nucleotides, (ii) more than one mutation of interest is present in the 3 or fewer nucleotides between the 3' ends of the primers and (iii) the product of the PCR reaction is such that each mutations gives a different restriction profile when at least one restriction enzyme is used to digest the PCR product and this restriction profile is different from that of the wild type sequence.

2. The method according to claim 1, wherein the 3' ends of the primers are separated by
   a) 3 nucleotides;
   b) 2 nucleotides;
   c) 1 nucleotide.

3. The method according to claim 1, wherein at least one of the pair of PCR primers is at least 30 nucleotides in length.

4. The method according to clam 3, wherein one of the pair of PCR primers is smaller than the other by at least 20bp.

5. The method according to claim 1, wherein at least one of said pair of PCR primers is used to introduce discriminatory restriction sites into the nucleotide sequence when used in a PCR reaction.

6. The method according to claim 1, wherein, when more than one mutation of interest is present, more than one restriction enzyme is used, the number of restriction enzymes corresponding to the number of mutations of interest plus one and
   (i) one of said restriction enzymes being able to digest the wild type sequence but not of the mutant sequence;
   (ii) each addition restriction enzyme being able to digest a single mutant sequence but not the wild type sequence.

7. The method of claim 1, wherein the point mutation or mutations of interest confer pesticidal resistance.

8. The method of claim 1, wherein the point mutation or point mutations of interest confer herbicide resistance.

9. The method of claim 1, wherein the point mutation or mutations of interest cause a biochemical or physiological change in an organism which results in disease.

* * * * *